US008569346B1

(12) United States Patent
Zeytin et al.

(10) Patent No.: US 8,569,346 B1
(45) Date of Patent: Oct. 29, 2013

(54) THIAZOLINE RING COMPOUNDS AS BOTULINUM ANTAGONISTS

(75) Inventors: Füsûn N. Zeytin, Del Mar, CA (US); Ward Tucker, Madison, WI (US)

(73) Assignee: Biomadison, Inc., Del Mar, CA (US)

( * ) Notice: Subject to any disclaimer, the term of this patent is extended or adjusted under 35 U.S.C. 154(b) by 136 days.

(21) Appl. No.: 12/904,360

(22) Filed: Oct. 14, 2010

Related U.S. Application Data

(60) Provisional application No. 61/251,505, filed on Oct. 14, 2009.

(51) Int. Cl.
*A61K 31/41* (2006.01)
*A61K 31/425* (2006.01)

(52) U.S. Cl.
USPC .......................................... 514/360; 514/373

(58) Field of Classification Search
USPC .................................. 514/360, 373
See application file for complete search history.

(56) References Cited

U.S. PATENT DOCUMENTS

| 7,574,340 B2 | 8/2009 | Bavari et al. | |
| 7,947,717 B2 * | 5/2011 | Pellecchia | 514/369 |
| 2007/0112049 A1 | 5/2007 | Bavari et al. | |

OTHER PUBLICATIONS

Capkova, K, et al., "Synthesis and Structure-Activity Relationships of Second Generation Hydroxamate Botulinum Neurotoxin A Protease Inhibitors", NIH Public Access, Bioorg Med Chem Lett., Dec. 1, 2007; 17(23): 6463-6466.

Burnett, J C, et al., "Inhibition of Metalloprotease Botulinum Serotype A from a Pseudo-peptide Binding Mode to a Small Molecule That Is Active in Primary Neurons", The Journal of Biological Chemistry, Feb. 16, 2007, vol. 282, No. 7, pp. 5004-5014.

Couesnon, A, et al., "Differential entry of botulinum neurotoxin A into neuronal and intestinal cells", Cellular Microbiology, 2009, vol. 11, No. 2, pp. 289-308.

Eubanks, L M, et al., "An in vitro and in vivo disconnect uncovered through high-throughput identification of botulinum neurotoxin A antagonists", PNAS, Feb. 20, 2007, vol. 104, No. 8, pp. 2602-2607.

Foster, K, et al., "142. Engineered toxins: New therapeutics", National Heart & Lung Institute, 2008, London, UK.

Foster, K, "Engineered toxins: New therapeutics", Toxicon, 2009, vol. 54, 587-592.

Siechen, S, et al., "Mechanical tension contributes to clustering of neurotransmitter vesicles at presynaptic terminals", PNAS, Aug. 4, 2009, vol. 106, No. 31, pp. 12611-12616.

Roxas-Duncan, V, et al., "Identification and Biochemical Characterization of Small-Molecule Inhibitors of *Clostridium botulinum* Neurotoxin Serotype A", Antimicrobial Agents and Chemotherapy, Aug. 2009, pp. 3478-3486.

* cited by examiner

*Primary Examiner* — Renee Claytor
(74) *Attorney, Agent, or Firm* — Fish & Associates, PC

(57) ABSTRACT

Compositions and methods for inhibiting BoNT protease activity are presented. In most preferred aspects, inhibitors comprise a thiol reactive group, a zinc binding group, a redox active group, an alkylating group, and/or an electrophilic Michael addition acceptor group. Particularly preferred inhibitors include an isothiazolone ring, a thiadiazolidine dione ring, a (hydro)quinone ring, an iminophenol group, and/or a hydrazonophenol group, and inhibit BoNT/A at μM and sub-μM concentrations.

3 Claims, 12 Drawing Sheets

Figure 1B

| Compound | Activation | More active in 1st or 2nd |
|---|---|---|
| (benzotriazole imine of 3,5-dichlorosalicylaldehyde) | 133.9 | 2nd |
| (N-benzyl imine of 3,5-dichlorosalicylaldehyde) | 138.7 | 1st |
| (4-chlorophenylthio-nitro-benzylidene rhodanine) | 132.9 | 2nd |
| (2,5-bis(furan-2-ylmethylene)cyclopentanone) | 146.9 | 2nd |
| (ethyl carbazate of 2,5-bis(2,2,2-trifluoroethoxy)acetophenone) | 220.5 | 1st |

Figure 2A

| Compound | Activation | More active in 1st or 2nd |
|---|---|---|
| (4-chloro-2-cyanophenyl biguanide structure) | 166.3 | 2nd |
| (benzimidazole-N=CH-3,5-dichloro-2-hydroxyphenyl structure) | 127.6 | 2nd |
| (3-cyclopropylmethyl-5-(2-chloro-6-methylphenyl)-1,2,4-thiadiazolidine-3,5-dione structure) | 144.1 | 2nd |
| (2,5-diiodo-1,4-benzoquinone structure) | 125.3 | 2nd |

Figure 2B

| Compound | Activation | More active in 1st or 2nd |
|---|---|---|
|  | 125.8 | 2nd |
|  | 133.5 | 2nd |
|  | 154.0 | 2nd |
|  | 148.4 | 2nd |

Exemplary Isothiazolone Compounds and Analogs

(A1-1)

(A1-2)

(A1-3)

(A1-4)

(A1-5)

(A1-6)

(A1-7)

(A1-8)

(A1-9)

(A1-10)

(A1-11)

Exemplary Thiadiazolidine Dione Compounds and Analogs

(A2-1)

(A2-2)

(A2-3)

(A2-4)

(A2-5)

Exemplary Quinone/Hydroquinone Compounds and Analogs

(B1-1)

(B1-2)

(B1-3)

(B1-4)

(B1-5)

(B1-6)

(B1-7)

Exemplary Iminophenol Compounds and Analogs

(C1-1)

(C1-2)

(C1-3)

(C1-4)

(C1-5)

(C1-6)

(C1-7)

(C1-8)

Exemplary Hydrazonophenol Compounds and Analogs

(C2-1)

(C2-2)

(C2-3)

(C2-4)

Exemplary Michael Acceptor Compounds

(D2-1)

(D2-2)

(D2-3)

(D2-4)

(D2-5)

THIAZOLINE RING COMPOUNDS AS BOTULINUM ANTAGONISTS

This application claims priority to our U.S. provisional patent application with the Ser. No. 61/251,505, which was filed Oct. 14, 2010.

FIELD OF THE INVENTION

The field of the invention is compositions and methods for protease inhibitors, and especially for Botulinum neurotoxins (BoNTs).

BACKGROUND OF THE INVENTION

Botulinum neurotoxins (BoNTs) are extremely toxic proteins and can be classified into distinct subgroups based, inter alia, on peptide sequence and substrate specificity. All of the naturally occurring BoNTs (BoNT/A-G) are composed of a heavy chain that mediates toxin entry into a target cell and a light chain with zinc-dependent protease activity that hydrolyzes selected SNARE proteins that mediate fusion of neurotransmitter vesicles to the membrane that forms part of the synaptic cleft. For example, the light chain of BoNT/A hydrolyzes with high specificity SNAP-25, which is required for vesicle-mediated exocytosis of acetylcholine into the synaptic cleft.

Unfortunately, therapeutic options for BoNT poisoning (e.g., immunoprophylactic vaccine, antitoxin or antibody administration, etc.) have proven less than ideal for various reasons. For example, vaccination typically results in relatively low antibody titers, while neutralizing proteins are often immunogenic. Still further, the therapeutic window of such options is generally limited to a small period as the BoNT is readily taken up into the neural cells. Therefore, development of various small molecule inhibitors of the light chain protease activity has gained considerable attention.

For example, various small-molecule compounds have recently been reported as light chain protease inhibitor, and most notably selected compounds that include a hydroxamate group (see e.g., Bioorg Med Chem Lett. 2007 December 1; 17(23): 6463-6466). However, at least some of these compounds are relatively toxic and thus failed to provide a meaningful antidote. Similarly, various quinolinol compounds were reported as relatively active protease inhibitors (see e.g., Antimicrobial Agents And Chemotherapy, August 2009, p. 3478-3486). However, such compounds tend to suffer from relatively poor solubility. In still further known approaches, the small molecule inhibitor NSC 240898 was designed based on docking data from pseudo-peptide mpp-RATKML, which is a known inhibitor of BoNT/A (U.S. Pat. App. No. US2007/0112049 or The Journal Of Biological Chemistry Vol. 282, NO. 7, pp. 5004-5014). While such approach provided at least a promising scaffold, the affinity of the NSC 240898 is less than desirable. Further screening data and lead compounds are provided elsewhere (see e.g., Proc Natl Acad Sci USA. 2007 February 20; 104(8): 2602-2607; J Appl Toxicol. 1999 December; 19 Suppl 1:S5-S11; U.S. Pat. No. 7,574, 340), however, most of the known compounds are either toxic or have a relatively weak activity.

As can be seen from the foregoing, there is a relatively wide diversity in structures that have at least some inhibitory activity against BoNT protease activity. However, all or almost all of the known compounds suffer from one or more disadvantages. Therefore, there is a continuing need for new and improved methods and compositions for inhibiting BoNT related protease activity.

SUMMARY OF THE INVENTION

The present invention is directed to compounds, compositions, and methods of inhibiting BoNT protease activity, and especially BoNT/A light chain protease activity. Most preferably, the compounds presented herein may not only serve as specific BoNT inhibitors, but also yield a scaffold for further improvement in inhibitory activity and/or specificity against one or more of BoNT/A-G.

In one aspect of the inventive subject matter, compounds with inhibitory activity include those that have a substructure that is or can generate a moiety selected from the group consisting of a thiol reactive group, and a zinc binding group, a redox active group, an alkylating group, and an electrophilic Michael addition acceptor group. Particularly preferred moieties include an isothiazolone ring, a thiadiazolidine dione ring, a quinone/hydroquinone ring, an iminophenol group, and/or a hydrazonophenol group, all of which are preferably substituted with one or more substituents. Therefore, and viewed from a different perspective, especially preferred compounds will have a structure according to any one of Formulae I-VI:

Formula I wherein Y is S, S=O, S(=O)$_2$, or N; R$_2$ is O or OH; and R$_1$, R$_3$, and R$_4$ are independently H, alkyl, alkenyl, alkaryl, aryl, heteroalkyl, and heteroaryl, wherein each of R$_1$, R$_3$, and R$_4$ may be optionally substituted with one or more substituents, and optionally wherein R$_3$ and R$_4$ may form ring, which may be a heterocyclic ring. It should further be noted that the heterocyclic ring formed by N, Y, and three carbon atoms may have one or more double bonds, and may or may not be aromatic. Most preferably, Y is S, R$_2$ is O, and R$_1$ is optionally substituted alkyl or aryl.

Formula II wherein Y is S, N, S=O, S(=O)$_2$, or N; and R$_1$ and R$_2$ are independently H, alkyl, alkenyl, alkaryl, aryl, heteroalkyl, and heteroaryl, wherein R$_1$ and/or R$_2$ may be optionally substituted with one or more substituents. It should once more be noted that the heterocyclic ring formed by N, Y, and two carbon atoms may have one or more double bonds, and may be aromatic. Most preferably, Y is S, and R$_1$ and R$_2$ are optionally substituted alkyl, alkaryl, or aryl.

Formula III wherein Q is =O or OH; and $Z_1$, $Z_2$, $Z_3$, and $Z_4$ are independently H or halogen. As noted before, the ring in Formula III may have one or more double bonds, and may be aromatic. Most preferably, Q is =O, and $Z_1$ and $Z_3$ are halogen, and $Z_2$ and $Z_4$ are hydrogen.

Formula IV wherein Q is OH; and $R_1$ and $R_2$ are independently H, alkyl, alkenyl, alkaryl, aryl, heteroalkyl, and heteroaryl, wherein $R_1$ and $R_2$ may together form a ring and may optionally be substituted with one or more substituents. W is H, =O, or OH, and $R_3$ is H, alkyl, alkenyl, alkaryl, aryl, heteroalkyl, or heteroaryl. The dashed line is an optional double bond. Most preferably, $R_3$ is aryl, W is H, $R_1$ and $R_2$ form an aromatic and optionally substituted ring.

Formula V wherein $R_1$ and $R_4$ are independently H, alkyl, alkenyl, alkaryl, aryl, heteroalkyl, and heteroaryl, each of which may be optionally substituted with one or more substituents; $R_2$ is =O or =S; and $R_3$ is alkyl, alkaryl, aryl, heteroalkyl, and heteroaryl, which may be substituted with one or more substituents. Most preferably, $R_1$ and $R_4$ are H, $R_2$ is =S, and $R_3$ is a substituted aryl or alkaryl.

Formula VI wherein $R_1$ and $R_4$ are independently H, alkaryl, aryl, heteroalkyl, and heteroaryl, each of which may be substituted, and wherein $R_2$ and $R_3$ are hydrogen or form together a five- or six-membered ring, which may optionally be substituted with one or more substituents. Most preferably, $R_1$ and $R_4$ are independently aryl or heteroaryl, and $R_2$ and $R_3$ form together a cyclopentyl or cyclohexyl ring.

In another aspect of the inventive subject matter, a method of inhibiting BoNT-A light chain activity will therefore comprise a step of contacting the BoNT-A light chain with at least one compound having a structure according to any one of Formulae VII-XIX as shown below, wherein the compound is optionally in form of a prodrug, a metabolite, or salt thereof, and wherein the compound present at a concentration effective to inhibit BoNT-A light chain activity. Most typically, the compound will be orally administered and/or injected into a mammal in need thereof, either as prophylactic measure or as a treatment upon exposure to BoNT-A.

Consequently, and viewed from a different perspective, pharmaceutical compositions are contemplated that comprise a pharmaceutically acceptable carrier and a compound having a structure according to any one of Formulae I-VI as shown above in an amount effective to inhibit BoNT-A light chain activity in a person to which the composition is administered. As noted before, the pharmaceutical composition is formulated as an injectable or inhalable composition.

Various objects, features, aspects and advantages of the present invention will become more apparent from the following detailed description of preferred embodiments of the invention.

BRIEF DESCRIPTION OF THE DRAWING

FIG. 1B is a graph illustrating dose response curves for inhibition by one exemplary compound in the presence of 1, 10, or 100 µM ZnCl2.

FIGS. 2A-2C depict exemplary compounds and test results for BoNT/A inhibition.

DETAILED DESCRIPTION

Figure 1A:
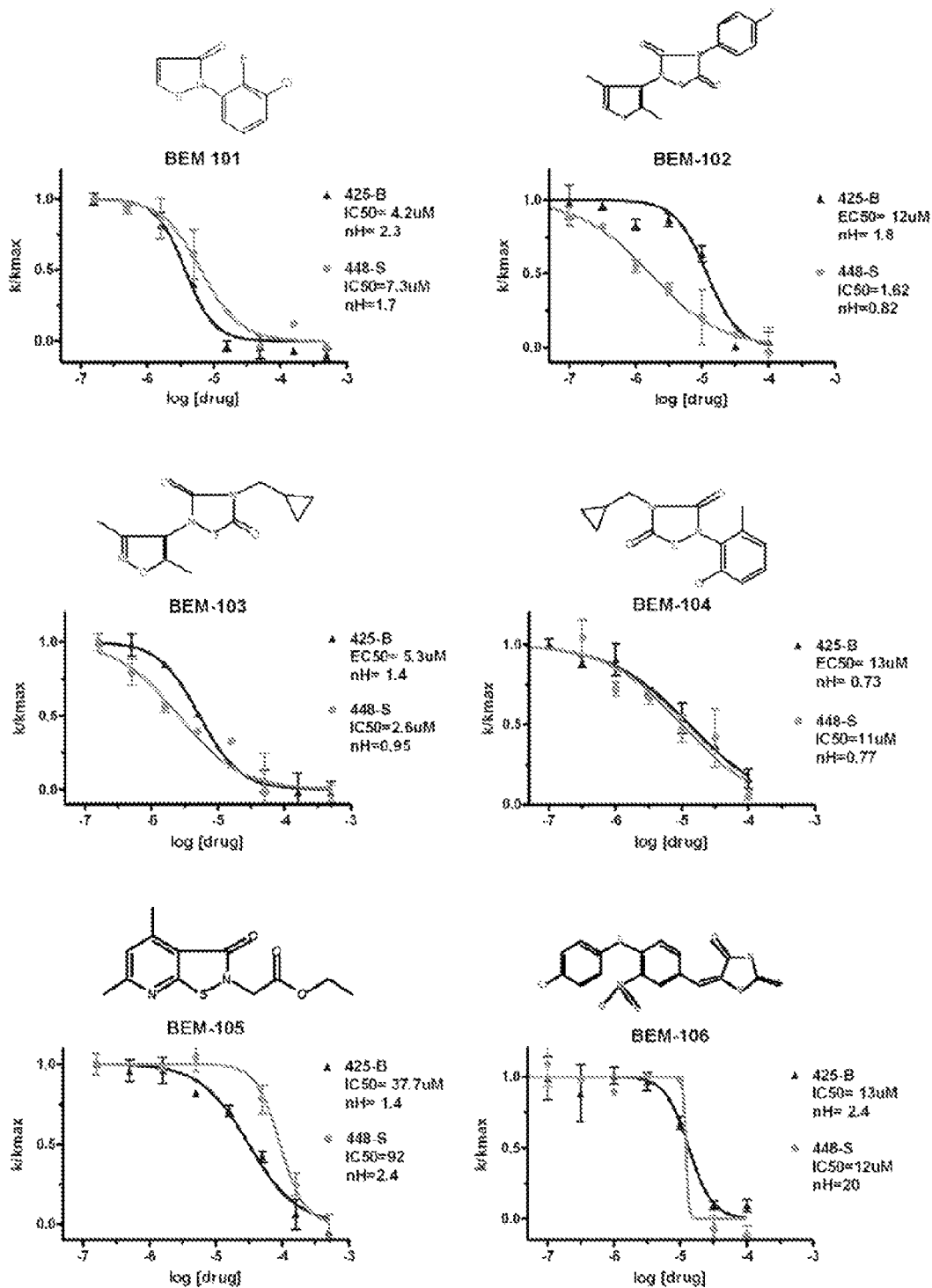
FIG. 1A is a set of graphs illustrating results for six exemplary thiazolinone compounds tested with a "short-form" and a "long-form" of BoNT/A LC.

The inventors have discovered various compounds with substantial inhibitory activity against BoNT protease activity, and especially BoNT/A light chain protease activity. Moreover, the inventors have also discovered that at least some of these compounds share one or more common structural elements that may contribute to the protease inhibitory activity, either directly via interaction with one or more functional groups and/or zinc in the light chain, or indirectly as scaffold or non-competitive or allosteric inhibitor.

A first set of compounds was identified using a screening assay of over 200 compounds that were previously selected in a primary screen of a commercially available compound library (Maybridge Hit-Finder, 14,400 Compound Cluster based library) using a FRET assay that employed CFP-SNAP25(141-206)-Venus as a substrate. Based on these findings and further considerations, especially contemplated compounds with inhibitory activity include those that have a substructure that is, or can generate a moiety that interferes with the catalytic activity of BoNT/A. For example, inhibitors may bind zinc from the active site, react with a thiol group of a cysteine (e.g., via disulfide bond formation, alkylation, Michael addition, nucleophilic attack, etc.), and/or may modify the protein or zinc via redox a reaction.

While numerous chemical moieties are known to allow for the above reactions, particularly preferred moieties include isothiazolone rings, thiadiazolidine dione rings, quinone, semiquinone, and hydroquinone rings, iminophenol groups, and hydrazonophenol group, all of which are typically substituted with one or more substituents to accommodate for improved binding and/or pharmacokinetic/pharmacodynamic properties.

For example, it is contemplated that compounds containing an isothiazolone ring may undergo a ring opening reaction to so form a free thiol or disulfides (Ye at al. J. Pharm. Biomed. Anal. 2000, 24, 273-280), which may react with a thiol group of the BoNT/A and/or which may also bind $Zn^{2+}$ from the BoNT/A. Therefore, in one especially preferred aspect, contemplated compounds will have a structure according to Formula I Formula I 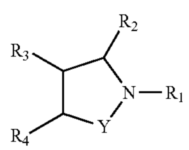 in which Y is S, S═O, S(═O)$_2$, or N; $R_2$ is O or OH; and $R_1$, $R_3$, and $R_4$ are independently H, alkyl, alkenyl, alkaryl, aryl, heteroalkyl, and heteroaryl, wherein each of $R_1$, $R_3$, and $R_4$ may be optionally substituted with one or more substituents, and optionally wherein $R_3$ and $R_4$ may form ring, which may be a heterocyclic ring. It should further be noted that the heterocyclic ring formed by N, Y, and three carbon atoms may have one or more double bonds, and may or may not be aromatic. Most preferably, Y is S, $R_2$ is O, and $R_1$ is optionally substituted alkyl or aryl.

Similarly, where the compound includes a thiadiazolidine dione ring, oxidation of the ring could once again lead to ring opening to so generate a reactive thiol, which could in turn interfere with the BoNT/A activity. Consequently, and in a further preferred aspect of the inventive subject matter, contemplated compounds will have a structure according to Formula II Formula II 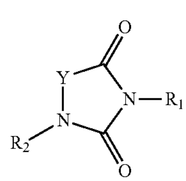 where Y is S, N, S═O, S(═O)$_2$, or N; and $R_1$ and $R_2$ are independently H, alkyl, alkenyl, alkaryl, aryl, heteroalkyl, and heteroaryl, wherein $R_1$ and/or $R_2$ may be optionally substituted with one or more substituents. It should once more be noted that the heterocyclic ring formed by N, Y, and two carbon atoms may have one or more double bonds, and may be aromatic. Most preferably, Y is S, and $R_1$ and $R_2$ are optionally substituted alkyl, alkaryl, or aryl.

In another example, where compounds include a quinone ring, it should be appreciated that such systems are not only redox active (lead to free radical generation) but also possess thiol reactivity, possibly via alkylation of a thiol group in a protein, and either mechanism or a combination of the two are contemplated. Thus, in yet another aspect of the inventive subject matter, particularly preferred compounds will have a structure according to Formula III Formula III 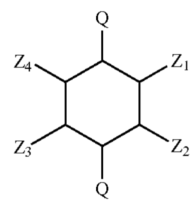 In which Q is ═O or OH; and $Z_1$, $Z_2$, $Z_3$, and $Z_4$ are independently H or halogen. As noted before, the ring in Formula III may have one or more double bonds, and may be aromatic. Most preferably, Q is ═O, and $Z_1$ and $Z_3$ are halogen, and $Z_2$ and $Z_4$ are hydrogen.

In a further example, compounds may include an iminophenol and/or hydrozonophenol group (or other Salen-type moiety), which is known to act as a Zn2+-binding motif. Most typically, such compounds will form a complex in which one metal atom is bound by two Salen-type compounds. Consequently, further especially preferred compounds will have a structure according to Formula IV Formula IV 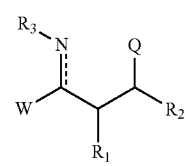 in which Q is OH; and $R_1$ and $R_2$ are independently H, alkyl, alkenyl, alkaryl, aryl, heteroalkyl, and heteroaryl, wherein $R_1$ and $R_2$ may together form a ring and may optionally be substituted with one or more substituents. W is H, ═O, or OH, and $R_3$ is H, alkyl, alkenyl, alkaryl, aryl, heteroalkyl, or heteroaryl. The dashed line is an optional double bond. Most preferably, $R_3$ is aryl, W is H, $R_1$ and $R_2$ form an aromatic and optionally substituted ring.

In a further example, compounds may include an alpha, beta-unsaturated carbonyl that may act as a Michael acceptor in a reaction that modifies a thiol group of a cysteine in the protease. Additionally, and depending on the particular structure of the compounds, such acceptors may further bind Zn2+ ions where an additional thiol group is present. Thus, preferred compounds will also include those having structures according to Formulae V and VI

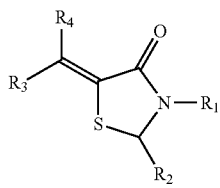

Formula V wherein $R_1$ and $R_4$ are independently H, alkyl, alkenyl, alkaryl, aryl, heteroalkyl, and heteroaryl, each of which may be optionally substituted with one or more substituents; $R_2$ is =O or =S; and $R_3$ is alkyl, alkaryl, aryl, heteroalkyl, and heteroaryl, which may be substituted with one or more substituents. Most preferably, $R_1$ and $R_4$ are H, $R_2$ is =S, and $R_3$ is a substituted aryl or alkaryl.

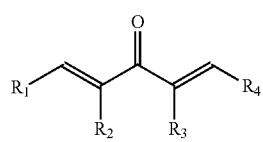

Formula VI wherein $R_1$ and $R_4$ are independently H, alkaryl, aryl, heteroalkyl, and heteroaryl, each of which may be substituted, and wherein $R_2$ and $R_3$ are hydrogen or form together a five- or six-membered ring, which may optionally be substituted with one or more substituents. Most preferably, $R_1$ and $R_4$ are independently aryl or heteroaryl, and $R_2$ and $R_3$ form together a cyclopentyl or cyclohexyl ring.

It should be noted that exemplary compounds and analogs thereof can be synthesized in a de novo approach, or starting from various commercially available compounds. Exemplary suitable commercially available compounds are depicted in FIGS. 3A-3G, which may be directly used as inhibitors and/or used as a scaffold for SAR studies to arrive at even more potent inhibitors. Therefore, it should be noted that the compounds presented herein may be used as a lead compound from which additional compounds are designed with even higher inhibitory effect and/or modified physicochemical and/or pharmacokinetic/dynamic parameters (e.g., solubility, metabolism, excretion, tissue distribution, etc.). For example, it should be noted that where the compounds have a hydrogen atom in a particular position, numerous substituents other than a hydrogen atom are also contemplated. It should also be recognized that not only hydrogen atoms may be substituted, but that also functional groups may be substituted with one or more substituents, which may in turn be substituted as well. For example, where a hydrogen atom in an alkyl is substituted with an amino group, one or both hydrogen atoms in the amino group may be substituted with another group (e.g., alkyl or alkenyl).

The term "substituted" as used herein refers to a replacement of an atom or a functional group (e.g., H, NH2, or OH) with another atom or functional group, and particularly contemplated functional groups include nucleophilic groups (e.g., —NH2, —OH, SH, —NC, etc.), electrophilic groups (e.g., C(O)OR, C(X)OH, etc.), polar groups (e.g., —OH), non-polar groups (e.g., aryl, alkyl, alkenyl, alkynyl, etc.), ionic groups (e.g., NH3+), and halogens (e.g., —F, —Cl). Further contemplated functional groups include NHCOR, NHCONH2, NHCSNH2, OCH2COOH, OCH2CONH2, OCH2CONHR, OC(Me)2COOH, OC(Me)2CONH2, NHCH2COOH, NHCH2CONH2, NHSO2R, NHSO2CF3, OCH2-heterocycles, PO3H, SO3H, (CH2)1-3COOH, CH=CHCOOH, O(CH2)1-4COOH, NHCOCH2CH(OH)COOH, CH(COOH)2, CH(PO3H)2, OCH2CH2CH2COOH, NHCHO, with R being an alkyl, halogen, or H. Moreover, and as already noted above, the term "substituted" also includes multiple degrees of substitution, and where multiple substituents are disclosed or claimed, the substituted compound can be independently substituted by one or more of the disclosed or claimed substituent moieties.

Thus, the term "functional group" and "substituent" are used interchangeably herein and refer to groups including nucleophilic groups (e.g., —NH2, —OH, SH, —NC, —CN etc.), electrophilic groups (e.g., C(O)OR, C(X)OH, C(Halogen)OR, etc.), polar groups (e.g., —OH), non-polar groups (e.g., aryl, alkyl, alkenyl, alkynyl, etc.), ionic groups (e.g., NH3+), and halogens, as well as NHCOR, NHCONH2, NHCSNH2, OCH2COOH, OCH2CONH2, OCH2CONHR, OC(Me)2COOH, OC(Me)2CONH2, NHCH2COOH, NHCH2CONH2, NHSO2R, NHSO2CF3, OCH2-heterocycles, PO3H, SO3H, (CH2)1-3COOH, CH=CHCOOH, O(CH2)1-4COOH, NHCOCH2CH(OH)COOH, CH(COOH)2, CH(PO3H)2, NHCHO, OCH2CH2CH2COOH, etc., with R being an alkyl, halogen, or H.

Moreover, it should be appreciated that the compounds according to the inventive subject matter may be modified to their corresponding bioisosteric compounds. For example, a hydrogen atom may be replaced by a fluorine atom, an ester may be replaced with a amide, or a phenyl ring with an aromatic ring having one or more heteroatoms. Additionally, it should be noted that one or more heteroatoms may be replaced with another heteroatom (e.g., a ring nitrogen may be replaced by a ring oxygen).

In still further contemplated aspects of the inventive subject matter, it should be recognized that contemplated compounds may be present in various forms, including stereoisomeric forms (e.g., diastereomers, enantiomers), tautomeric forms (e.g., keto-enol tautomers), and may exhibit optical activity (e.g., (+) or (−) rotation), or may be present as salts, hydrates, oligomers, polymers, prodrugs, or metabolites, all of which are expressly contemplated herein. Moreover, contemplated compounds may further be present as isolated compounds, as mixtures of pure compounds, and/or as mixtures of a pure compound with an isolate. Where contemplated compounds are prepared as a prodrug, it is generally preferred that the prodrug has increased bioavailability to a target cell, and especially neural cell.

Contemplated prodrugs for the compounds presented herein include those having modifications as described in, for example, Fleisher et al., Advanced Drug Delivery Reviews 19 (1996) 115-130; Design of Prodrugs, H. Bundgaard, Ed., Elsevier, 1985; H. Bundgaard, Drugs of the Future 16 (1991) 443; Saulnier et al., Bioorg. Med. Chem. Lett. 4 (1994) 1985; Safadi et al., Pharmaceutical Res. 10 (1993) 1350. Especially contemplated prodrugs include ester prodrugs of acid groups, and acyl prodrugs and carbamate prodrugs of acylatable nitrogen-containing groups (e.g., amino group, amidino group or guanidino group). For example, in the acyl prodrug or carbamate prodrug, a hydrogen atom on a nitrogen atom is replaced by an acyl group or carbamate group. These prodrugs can be prepared by customary methods familiar to those skilled in the art for the preparation of acylamines and carbamates.

Similarly, it should also be appreciated that contemplated compounds may also be prepared as metabolites. Metabolites will typically be identified by use of radiolabeled precursor compounds that are then isolated from selected tissues and characterized by manners well known in the art. The nature of the metabolite may vary significantly, however, especially preferred metabolites include glucuronidated forms, hydroxylated (or otherwise oxidized) forms, etc. Additional metabolic modifications include ring openings and esterifications.

In a further especially contemplated aspect, and without wishing to be bound by any particular theory or hypothesis, the inventors noted a thiazolinone ring moiety or similar moiety may have one or more modes of action that are particularly desirable for BoNT light chain inhibition. For example, in one mode of action, it should be noted that the compounds presented herein may act as a metal chelating or complexing agent, wherein the metal chelating or complexing activity may be present at or near the active site or in the proximity or microenvironment of the light chain. Alternatively, or additionally, it is contemplated that the thiazolinone ring-containing compounds may be oxidized in the cell to so form a thiol-containing compound with a hydroxamate group, which has been previously shown to have (in at least certain compounds) inhibitory activity. Consequently, it is contemplated that the compounds presented herein may act as competitive inhibitors, as non-competitive inhibitors, and/or as allosteric inhibitors, and/or even act as a metal chelating or complexing agent.

Upon more detailed analysis of compounds having protease inhibitory activity, the inventors noticed that several of the compounds with activity had some form of thiazoline ring moiety. Consequently, it is noted that the thiazoline ring/thiazolinone system represents a very high proportion of the compounds with protease inhibitory activity. While not wishing to be bound by any theory or hypothesis, it is thought that the S—N bond within the thiazoline ring/thiazolinone system is sensitive to oxidation, thus allowing for ring opening and formation of a free sulfhydryl group and a hydroxamate group. It is thus contemplated that such structural combination would result in a molecule that can interact strongly with zinc, either within the active site of the enzyme or by directly chelating the free zinc.

As can also be taken from the experimental data below, the compounds according to the inventive subject matter may exhibit immediate activity, or require some pre-incubation with the protease (which may be reflective of oxidation of the compound, induction of conformational change of the protease, kinetic of metal chelation, etc.). It was observed that most of the above-noted compounds were more potent in the $2^{nd}$ experiment compared to the $1^{st}$ (i.e. more potent the experiment where the compound was pre-incubated with the enzyme). This might suggest that the time of incubation with the enzyme is important for efficient inhibition with this class of compounds. The necessity of pre-incubation may suggest there may an additional reaction (e.g., the opening of the ring) that precedes binding to the active site of the enzyme, or that there is 2-step (or higher grade) reaction occurring between the inhibitor and the enzyme that requires longer co-incubation of the inhibitor with the enzyme. An additional possibility is that these structures are chelating zinc directly at the active site or microenvironment, and the zinc chelation step requires a co-incubation of the enzyme with the compound. Thus, it should be noted that the compounds and compositions presented herein may also be suitable for inhibition of BoNT proteases other than BoNT/A (i.e., BoNT/B-G).

In yet another preferred aspect, the inventors contemplate therapeutic and/or prophylactic compositions in which the compounds of the inventive subject matter are administered to a subject (preferably human) to counteract the effects of BoNT (and especially BoNT-A), which may have been introduced into the subject by ingestion (e.g., via food-borne pathogen), inhalation (e.g., aerosolized as biological agent), and/or injection (e.g., via cosmetic procedure). Therefore, contemplated pharmaceutical compositions will especially include those where contemplated compounds (and additional pharmaceutically active ingredients) are provided with a pharmaceutically acceptable carrier, wherein contemplated compounds are preferably present at a concentration effective to reduce or even abolish protease activity of BoNT-A LC in a cell or organ.

Depending on the particular use and structure, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro will generally be between 0.1 nM and 500 microM, more typically between 50 nM and 400 microM, and most typically between 100 nM and 200 microM.

Furthermore, it should be recognized that all formulations are deemed suitable for use herein and especially include oral and parenteral formulations. For example, for oral administration, contemplated compositions may be in the form of a tablet, capsule, suspension, or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier. In especially preferred aspects, it is contemplated that the formulation is suitable for injection or administration via aerosol or for intrathecal administration. Consequently, especially suitable formulations may be sterile (preferably aqueous) solutions for injection (e.g., as an injectable solution, suspension, or emulsion). In still further contemplated formulations, contemplated compounds may be formulated for aerosol delivery (e.g., micropowderized, coated onto a dispersible carrier, dissolved in atomizable solvent, etc.), or formulated in solid form as a tablet or capsule (with suitable carrier, disintegrant, etc.).

Consequently, it should be appreciated that the choice of the particular formulation and carrier will at least in part depend on the specific use and type of compound. There are numerous manners of drug formulation known in the art, and all of those are deemed suitable for use herein (see e.g., Pharmaceutical Preformulation and Formulation: A Practical Guide from Candidate Drug Selection to Commercial Dosage Form by Mark Gibson; Informa HealthCare, ISBN: 1574911201; or Advanced Drug Formulation Design to Optimize Therapeutic Outcomes by Robert O. Williams, David R. Taft, and Jason T. McConville; Informa HealthCare; ISBN: 1420043870).

For therapeutic or prophylactic purposes, contemplated compounds are ordinarily combined with one or more excipients appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

Additionally, and depending on the particular purpose, it should be recognized that contemplated compounds may be combined (in vivo or in a pharmaceutical formulation or administration regimen) with at least one other pharmaceutically active ingredient, and especially contemplated other ingredients. Concentrations of second pharmaceutically active ingredients are typically at or preferably below those recommended for stand-alone administration, however, higher concentrations are also deemed suitable for use herein.

Experiments

Initial screening revealed that 235 compounds of a commercially available library (the 14,400 compound Maybridge library) had inhibitory activity against BoNT/A LC light chain protease activity using CFP-SNAP25(141-206)-Venus as a substrate. Each of the identified 235 compounds was then tested in two separate experiments, with a single well for each compound in each experiment. Experiments used BoNT/A LC (2 nM in the first experiment, 1.5 nM in the second) and 0.8 uM CFP-SNAP25(141-206)-Venus as the substrate substantially following standard conditions known in the art. The two separate experiments were performed as follows:

Experiment 1 (No pre-incubation): 5 ul of 1 mM compound was aliquoted into 85 ul of buffer (50 mM HEPES 7.4, 0.05% Tween20, 1 mg/ml BSA). Two separate fluorescence emission wavelength scans was performed on each compound, one at 321 nm (SNAPtide) and one at 434 nm (CFP-Venus) excitation wavelengths. 10 ul of CFP-Venus substrate (0.8 uM final concentration) was then added to the compound solution, and the pre-experiment 434ex:470em/527em values determined for the substrate: compound mixture. 10 ul of BoNT/A LC (2 nM final) was added to the substrate-compound mixture, and the plate was loaded onto the plate reader.

Experiment 2 (Pre-incubation): Similar to Experiment 1, except 5 ul of 1 mM of each compound were directly diluted into 95 ul of BoNT/A LC (1.5 nM) for 15 minutes prior to adding 10 ul of CFP-YFP substrate (0.8 uM final concentration). No wavelength scan was performed, and pre-read values determined in Experiment 1 were used as pre-read values for Experiment 2.

Plate reader fluorescence measurements were made at 1 minute intervals, and the rate determined from slope of the line through the first 3 measurements. The initial rate of substrate cleavage was determined in the presence of compound and compared to control reactions on the same plate with no compound. Compounds resulting in >20% change in activity were considered "hits". A total of 26 compounds had activity in at least one of the two experiments (24 inhibitors and 2 enhancers of activity). Of the 26, six compounds inhibited BoNT/A LC activity in both assays, which are particularly preferred leads.

Figure 1B:
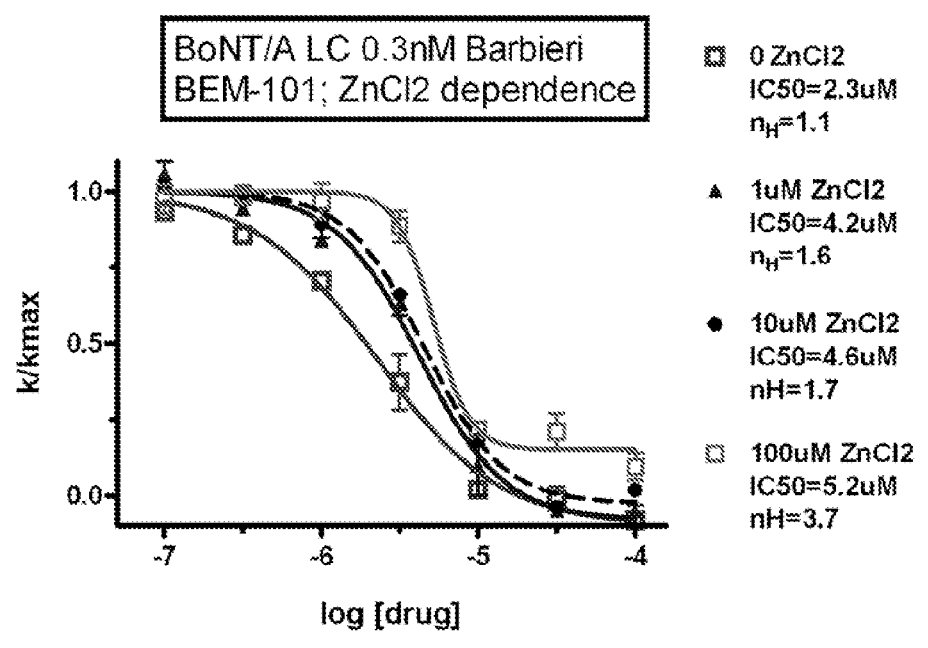

FIG. 1A shows selected results of experiments performed with six exemplary thiazolinone compounds that were identified earlier. In general, the thiazolinones gave similar IC50 values for both enzymes. Most of the experiments resulted in Hill numbers greater than 1.0, suggesting non-competitive inhibition. The steep Hill slopes suggest the compounds could be acting via zinc chelation. To determine if this is the case, dose-response curves for BEM-101 at three different concentrations of ZnCl2 were performed. Although the IC50 did not change significantly in the presence of ZnCl2, the Hill numbers increased significantly suggesting a partial ZnCl2 dependence. FIG. 1B shows typical dose response curves demonstrating inhibition by an exemplary compound (here: BEM-101) in the presence of 1, 10, or 100 uM ZnCl2, which suggests at least partial Zn dependence.

Figure 2C:
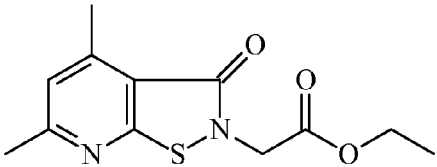
Figure 2C:
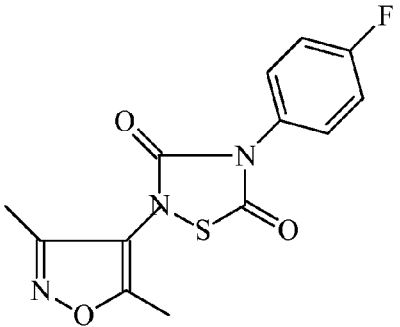
Figure 2C:
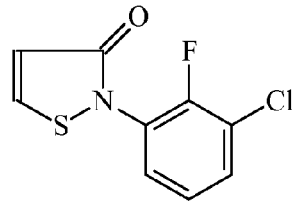
Figure 2C:
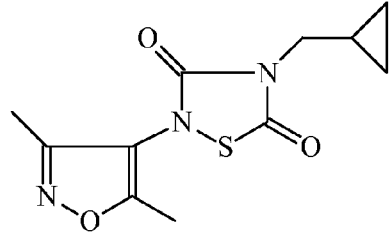
Figure 3A:
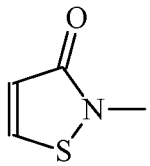
FIG. 3A depicts exemplary commercially available isothiazolone compounds and analogs suitable for use as BoNT/A inhibitors.
Figure 3A:
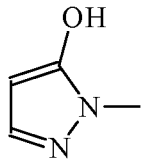
Figure 3A:
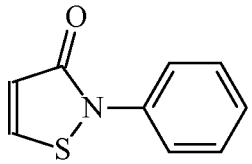
Figure 3A:
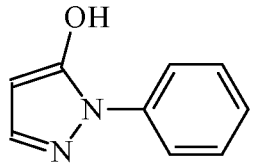
Figure 3A:
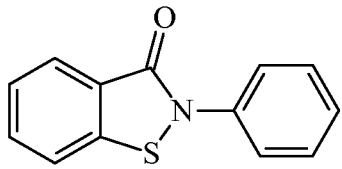
Figure 3A:
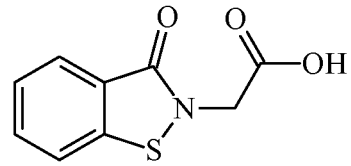
Figure 3A:
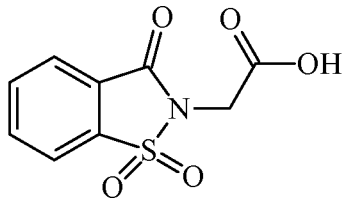
Figure 3A:
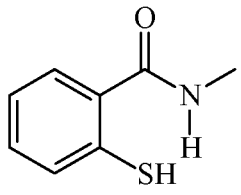
Figure 3A:
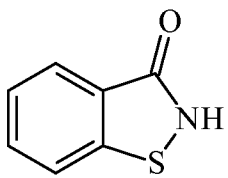
Figure 3A:
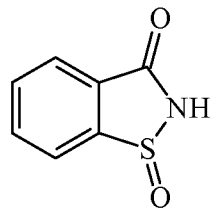
Figure 3A:
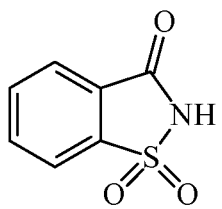
Figure 3B:
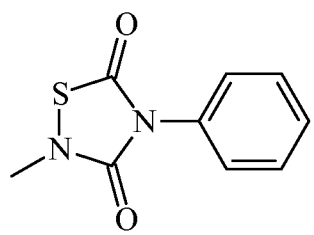
FIG. 3B depicts exemplary commercially available thiadiazolidine dione compounds and analogs suitable for use as BoNT/A inhibitors.
Figure 3B:
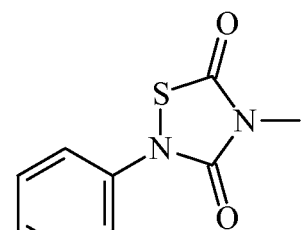
Figure 3B:
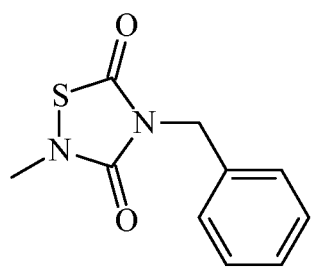
Figure 3B:
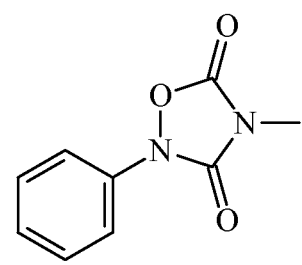
Figure 3B:
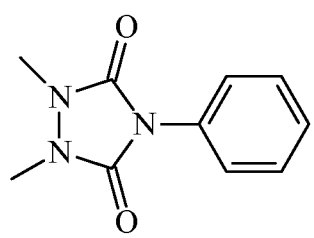
Figure 3C:
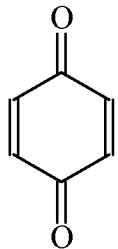
FIG. 3C depicts exemplary commercially available quinone/hydroquinone compounds and analogs suitable for use as BoNT/A inhibitors.
Figure 3C:
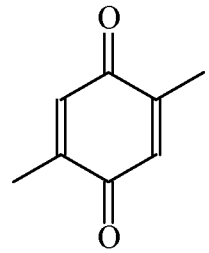
Figure 3C:
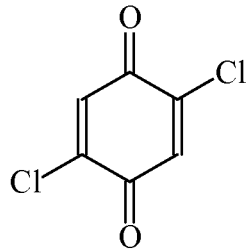
Figure 3C:
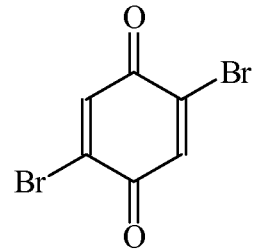
Figure 3C:
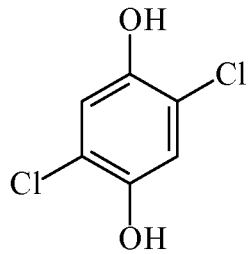
Figure 3C:
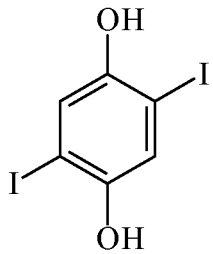
Figure 3C:
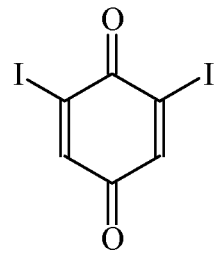
Figure 3D:
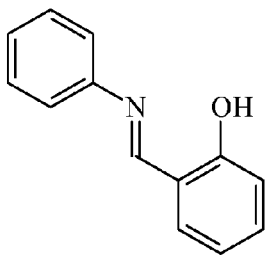
FIG. 3D depicts exemplary commercially available iminophenol compounds and analogs suitable for use as BoNT/A inhibitors.
Figure 3D:
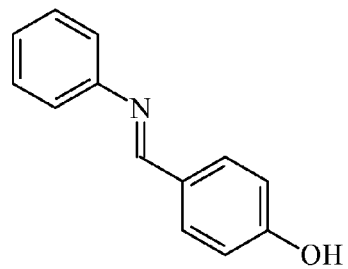
Figure 3D:
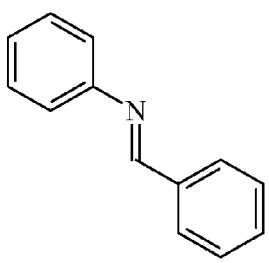
Figure 3D:
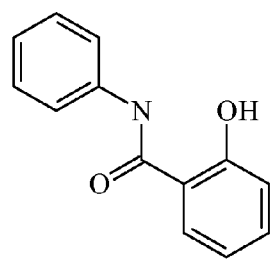
Figure 3D:
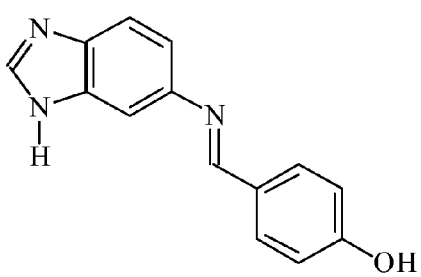
Figure 3D:
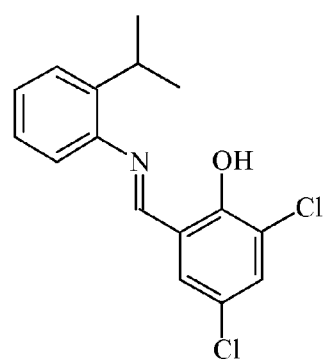
Figure 3D:
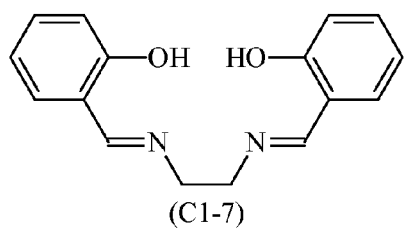
Figure 3D:
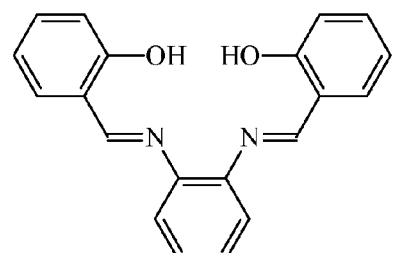
Figure 3E:
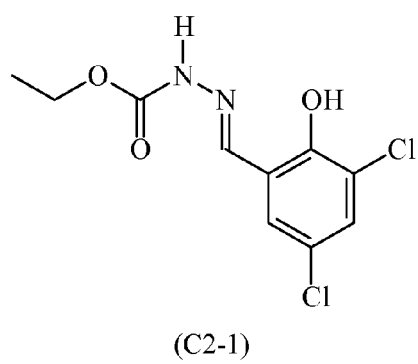
FIG. 3E depicts exemplary commercially available hydrazonophenol compounds and analogs suitable for use as BoNT/A inhibitors.
Figure 3E:
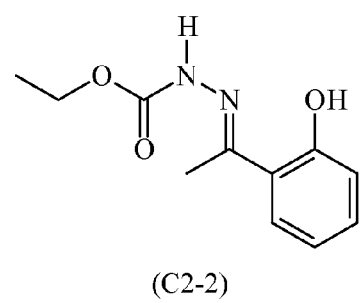
Figure 3E:
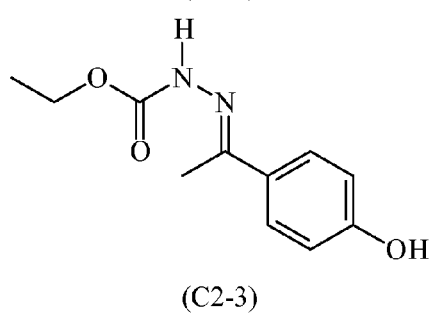
Figure 3E:
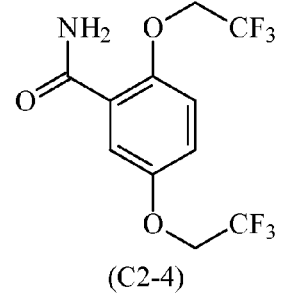
Figure 3F:
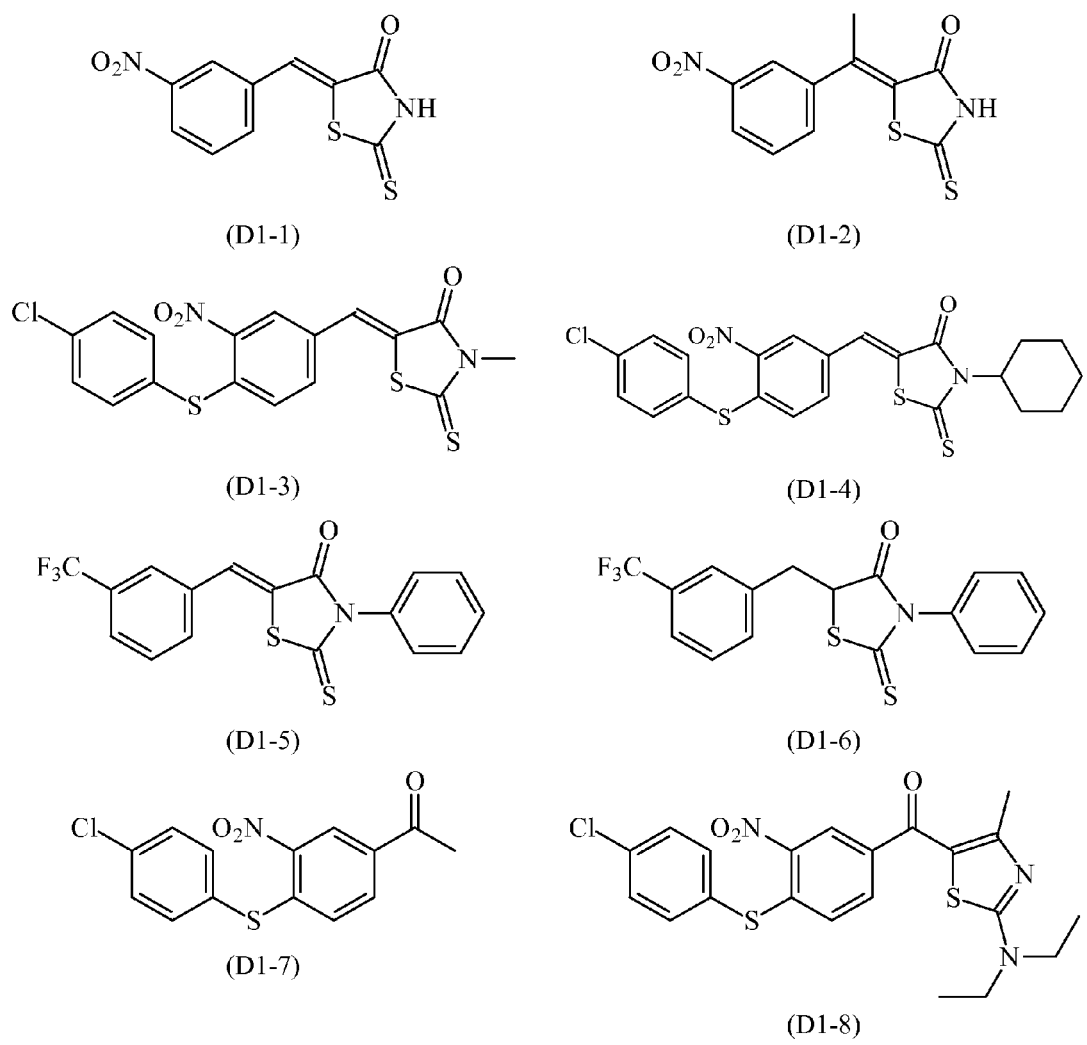
FIG. 3F depicts exemplary commercially available rhodanine compounds and analogs suitable for use as BoNT/A inhibitors.
Figure 3G:
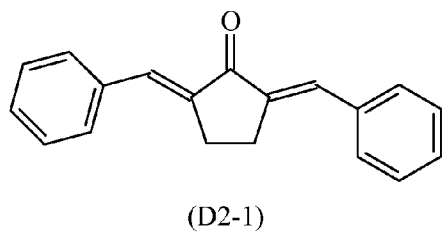
FIG. 3G depicts exemplary commercially available Michael acceptor compounds suitable for use as BoNT/A inhibitors.
Figure 3G:
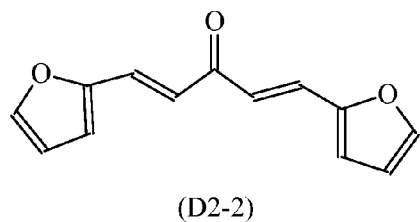
Figure 3G:
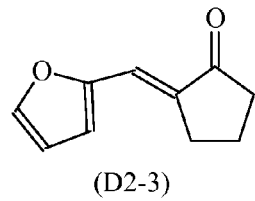
Figure 3G:
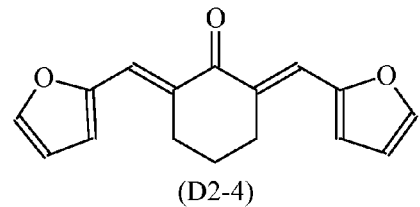
Figure 3G:
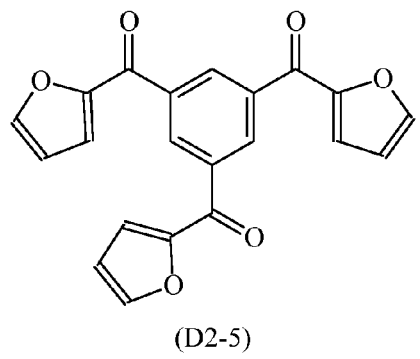

Further exemplary results are shown in FIGS. 2A-2C. Here, the first column shows the particular compound used, and the second column indicates the % of control signal during the high throughput primary screen. In this assay, BoNT/A activity is detected by a loss in the emission (527/470 nm) ratio value. An inhibitor of BoNT/A will thus have a higher emission ratio value. In all experiments, 50 µM inhibitor concentration was used. The third column states if the inhibitory activity was higher without pre-incubation ($1^{st}$ experiment) or with pre-incubation ($2^{nd}$ experiment).

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of inhibiting BoNT-A light chain activity comprising a step of contacting the BoNT-A light chain with a compound having a structure according to Formula 1:

Formula I wherein Y is S; $R_2$ is =O; $R_1$ is an optionally substituted alkyl or aryl; $R_3$, and $R_4$ are independently H, alkyl, alkenyl, alkaryl, aryl, heteroalkyl, or heteroaryl, wherein each of $R_3$ and $R_4$ may be optionally substituted with one or more substituents, wherein $R_3$ and $R_4$ may optionally form a ring, which may be a heterocyclic ring, and wherein the heterocyclic ring that includes N and Y in Formula I optionally has one or more double bonds.

2. The method of claim 1 wherein the step of contacting comprises oral administration to or injection of the compound into a subject affected with BoNT-A.

3. The method of claim 2 wherein administration or injection of the compound is performed as prophylactic measure.

* * * * *